United States Patent [19]

Pucci et al.

[11] Patent Number: 4,877,634
[45] Date of Patent: Oct. 31, 1989

[54] FOOD PRODUCT CONTAINING NOVEL DRIED COMPOSITIONS WITH POLYSACCHARIDES

[75] Inventors: Michael J. Pucci, Sarasota; Blair S. Kunka, Bradenton, both of Fla.

[73] Assignee: Microlife Technics, Inc., Sarasota, Fla.

[21] Appl. No.: 238,415

[22] Filed: Aug. 31, 1988

Related U.S. Application Data

[62] Division of Ser. No. 68,435, Jul. 1, 1987, Pat. No. 4,855,149.

[51] Int. Cl.$^4$ .................. A23C 9/154; A23G 9/00; A23L 1/24
[52] U.S. Cl. .................... 426/531; 426/580; 426/602; 426/565; 426/583; 426/658
[58] Field of Search .............. 426/34, 48, 531, 564, 426/658, 43, 61, 580, 602, 565, 583; 435/101

[56] References Cited

U.S. PATENT DOCUMENTS 4,416,905 11/1983 Landstedt et al. ................. 426/43

OTHER PUBLICATIONS

Schwartz et al., Appl. Environ. Microbiol. 48: 678–679 (1984).
Lawford et al., Biotechnol. Bioeng. 21: 1121–1131 (1979).
Kirk–Othmer 15: 439–447 (1981).
Niinobe et al., Nippon Nogeikagaku Kaishi 46: 81–88 (1972).
Preobrazhenskaya, M. E. et al., Prikladnaya Biokhimiya i Mikrobiolog. 10: 539–546 (1974).
Jeanes, A., ACS Symp. SEr. 45: 284–298 (1977).
Cottrell et al., Dev. Ind. Microbiol. 19: 117–131 (1978).

*Primary Examiner*—Marianne Cintins
*Attorney, Agent, or Firm*—Ian C. McLeod

[57] ABSTRACT

Novel dried compositions containing polysaccharides (dextrans and levans) derived using a Leuconostoc to ferment sucrose to produce the polysaccharides are described. In particular, dried compositions incorporating milk solids or other drying aids to facilitate drying and rehydration of the polysaccharides are described. The compositions are useful as quality (e.g. texture, stability or thickness) improvers for foods.

7 Claims, No Drawings

FOOD PRODUCT CONTAINING NOVEL DRIED COMPOSITIONS WITH POLYSACCHARIDES

This is a divisional of co-pending application Ser. No. 068,435 filed on July 1, 1987; now U.S. Pat. No. 4,855,149.

BACKGROUND OF THE INVENTION (1) Field of the Invention

The present invention relates to a method for producing novel dried compositions containing polysaccharides, particularly dextrans and levans. In particular the present invention relates to powdered compositions containing milk solids mixed with the polysaccharides which hydrate to form thickened aqueous solutions and which are particularly useful as edible quality improvers (e.g. stability, thickeners and/or texture) for foods.

(2) Prior Art

Dextrans are glucose polymers synthesized by several genera of bacteria including *Streptococcus, Lactobacillus,* and *Leuconostoc* (Schwartz, R. D., and E. A. Bodie, Appl. Environ Microbiol. 48:678–679 (1984); and Lawford, G. R., A. Kligerman, and T. Williams, Biotechnol. Bioeng. 21:1121–1131 (1979)). They are generally referred to as "microbial polysaccharides" (Kirk-Othmer 15:439–447 (1981)) Synthesis occurs via dextransucrase enzymes which are primarily extracellular. Dextran molecular weights range from $1.5 \times 10^4$ to $2 \times 10^7$ and higher (Schwartz, R. D., and E. A. Bodie, Appl Environ Microbiol. 48:678–679 (1984)). Dextrans consist of primarily alpha 1,6 linkages but alpha 1,4, alpha 1,2, and alpha 1,3 bonds are also known (Niinobe, M. and T. Kobayashi, Nippon Nogeikagaku Kaishi 46:81–88 (1972)). The extent of branching affects water solubility and other properties. Dextrans are presently used in a variety of industries; however, although the potential exists, uses of dextrans in the food industry are limited at present because of the difficulty in providing a useful dried product which rehydrates in water to produce a suitably thick solution (Jeanes, A., ACS Symp. Ser. 45:284–298 (1977)).

Dextran synthesis has probably been most widely studied in the genera Leuconostoc, particularly in *L. mesenteroides* (Lawford, G. R., A. Kligerman, and T. Williams, Biotechnol. Bioeng. 21:1121–1131 (1979); Niinobe, M. and T. Kobayashi, Nippon Nogeikagaku Kaishi 46:81–88 (1972); and Preobrazhenskaya, M.E. and N. A.Danilova., Prikladnaya Biokhimiya i Mikrobiologiya 10:539–546 (1974)). Leuconostoc sp. offer several advantages. First, they are unable to metabolize either dextrans (they contain no dextranases) or sucrose (no invertases or sucrose phosphorylases) (Jeanes, A., ACS Symp. Ser. 45:284–298 (1977)). Also, many Leuconostoc strains are prolific producers of sucrose-inducible extracellular dextransucrases and are, therefore, abundant producers of dextrans. Leuconostocs are used in foods. Finally, they are able to metabolize fructose, which is the byproduct of dextran synthesis, is an energy source. In some instances they can also produce levans (polyfructoses) by the action of levan sucrase.

Although dextrans presently have a variety of uses, few of these are in the food industry. One involves using dextran gel-filtration processes to concentrate or recover proteins from liquid wastes such as whey and cereal waste streams (Jeanes, A., ACS Symp. Ser. 45:284–298 (1977)).

OBJECTS

It is therefore an object of the present invention to provide dried polysaccharide-containing compositions derived from Leuconostoc sp. which rehydrate in water. Further it is an object of the present invention to provide a method for producing the dried compositions. Further still it is an object of the present invention to provide compositions which are useful as quality improvers for foods. These and other objects will become increasingly apparent by reference to the following description.

GENERAL DESCRIPTION

The present invention relates to a dried composition, particularly useful as a quality improver for foods, which comprises in admixture: a finely divided food grade drying aid and polysaccharides derived by fermenting an aqueous growth medium comprising sucrose with a Leuconostoc which produces substantially water rehydratable polysaccharides from the sucrose until the sucrose is essentially depleted and then drying the aqueous mixture to a powder with the drying aid. Preferably the dried composition contains at least about 7 percent and preferably between about 10 and 70 percent by weight of the drying aid. The present invention also relates to a method for forming a dried composition, particularly useful as an edible quality improver for foods, which comprises: providing an aqueous growth medium containing sucrose; fermenting with a Leuconostoc which produces substantially rehydratable polysaccharides in the growth medium in order to produce the polysaccharides in the growth medium until the sucrose is essentially depleted; and drying the growth medium to produce the dried composition with the polysaccharides.

The phrase "quality improver" means to improve the thickness, stability or texture and the like of a solid or liquid food product.

The phrase "drying aid" means a food grade, powdered, water absorbing material which when added to the polysaccharides in the growth medium results in a flowable, dried polysaccharide powder. Such aids include cellulose, silicates, casein, lactalbumin, NFDM, which is preferred, and other known food grade materials.

The phrase "milk solids" means the solids in fluid milk, condensed milk, NFDM, casein, whey and the like. Essentially milk solids can be any milk product containing casein or casein itself.

The preferred Leuconostoc sp. is *Leuconostoc dextranicum*. Most preferred is *Leuconostoc dextranicum* NRRL-B-18132 which is available from the Northern Regional Research Laboratory in Peoria, Illinois upon request by name and number. Other Leuconostoc and strains of *L. dextranicum* can be used, preferably those which are known to be acceptable in foods.

The growth medium contains sucrose. Preferably between about 5 and 15 percent sucrose by weight of the growth medium is used. More sucrose tends to be toxic to the Leuconostoc and less is ineffective.

The Leuconostoc are preferably grown in an aqueous growth medium containing milk solids which enhance the production of the polysaccharides and aid in drying. The milk solids are preferably derived from skim milk. The growth medium preferably contains between about 4% and 15% by weight of milk solids not fat.

Milk solids are very much preferred for drying the fermented polysaccharide containing growth medium. Fluid condensed milk, skim milk or NFDM can be used in the growth medium to provide the milk solids for drying. Also milk solids can be added as a supplement after the fermentation. In any event, the final dried composition preferably contains between about 10 and 70 percent by weight milk solids.

Preferably the fermentation is conducted at between about 15° C. and 35° C. These temperatures provide good production of the polysaccharides The fermented growth medium can be dried in any manner; however spray drying is preferred. The dried composition preferably contains between about 1 and 5 percent by weight moisture

SPECIFIC DESCRIPTION

The present invention particularly relates to dextran synthesis by *Leuconostoc dextranicum* NRRL-B-18132. This strain is an abundant producer of dextran and levan in admixture both in the laboratory and under production conditions. The dextran and levan mixture was harvested directly from a growth medium by spray drying. A high degree of viscosity was obtained when the dried compositions were rehydrated. The dextran and levan mixture is useful in food applications as a quality improver (thickness, stability and/or texture).

EXAMPLE 1

Strain and Growth Conditions. *Leuconostoc dextranicum* NRRL-B-18132 was grown in three different media: sucrose-salts, non-fat dry milk (NFDM)-sucrose, and whey sucrose. The sucrose-salts medium (Schwartz, R.D., and E. A. Bodie., Appl. Environ. Microbiol. 48:678–679 (1984)), consisted of 0.25% yeast extract, 0.5% $K_2HPO_4$, 0.01% $MgSO_4$, 1.0% casein hydrolysate, and 10% sucrose by weight. The whey-sucrose medium(1) contained 4% whey, 0.1% $K_2HPO_4$, 0.04% yeast extract, and 10% sucrose by weight. For the above two media, the sucrose was autoclaved separately and added after cooling. The NFDM-sucrose medium consisted of 15% NFDM and 10% sucrose by weight. The NFDM-sucrose mixture was steamed for 30 minutes at 95° C. for the purpose of pasteurization. Fermentations were performed without adding air or oxygen in a Bio-Flo Fermenter (New Brunswick Scientific Co.) with an agitation speed of 200 rpm. Temperature was maintained at 25° C. and pH was maintained at 6.0 by addition of 1N NaOH.

Purification. Dextran from *L. dextranicum* NRRL-B-18132 was purified using a method adapted from one used to isolate xanthan gums. (Cortell, I. W., and K. S. Kang, Dev. Ind. Microbiol. 19:117–131 (1978)). *L. dextranicum* NRRL-B-18132 was grown for 48 hrs. at 24° C in a one liter fermenter in sucrose-salts medium. The culture then was harvested and two volumes of isopropanol were added and mixed thoroughly. This solution was allowed to equilibrate at 4° C. for 18 hours. The solution and resulting precipitate then were filtered through a Buchner funnel using Whatman No. 1 filter paper. The precipitate was then dried under vacuum with desiccant for 48 hours. The dried precipitate then was heated in an oven for 4 hours at 60° C. to evaporate residual isopropanol. The precipitate then was weighed and crushed into fine off-white powder using a mortar and pestle. The dextran was analyzed and found to be 80% dextran and 20% levan (polyfructose). The latter polysaccharide may contribute to the unique properties of the preferred dried composition of the present invention.

EXAMPLE 2

Establishment of growth conditions. *Leuconostoc dextranicum* NRRL-B-18132 was grown in a sucrose-salts medium and the culture was examined visually for increases in viscosity at 24 and 48 hours. The 100 ml culture was incubated at 24° C. At both 24 and 48hrs., the culture appeared highly viscous with a slimy layer coating the bottom of the flask. Viscosity appeared to increase over time and the experiment was repeated at 32° C. with similar results.

*L. dextranicum* NRRL-B-18132 culture growth was scaled up in a one liter fermenter. The strain was grown in both sucrose-salts and whey-sucrose media. After 45 hours, the cultures were harvested and then lyophilized for 48 hours. The resultant dried products were spongy and could not be rehydrated which indicated that the dextran-levan was affected adversely by the lyophilization in these media. The yields were approximately 100 g/l.

*L. dextranicum* NRRL-B-18132 culture was scaled up in a 10 liters fermenter in the three different media: sucrose-salts, whey-sucrose, and NFDM-sucrose. The polysaccharides were harvested from these cultures by spray drying. In the case of the sucrose-salts and the whey-sucrose media, additional NFDM had to be added as a drying aid to facilitate the drying process and counteract effects from residual sucrose. Samples from each of the three cultures were taken prior to drying and the percent solids were determined using a hand held refractometer. The results were: sucrose-salts, 18.5% solids; NFDM-sucrose, 26.8% solids; and whey-sucrose 23% solids. The spray-died powders were reconstituted to the above percent solids concentrations and viscosities were examined visually. The Leuconostoc grown in the NFDM-sucrose growth medium regained the best viscosity when rehydrated and this medium was chosen for use in further large scale studies.

To determine the viscosity of the polysaccharide mixture as a function of concentration, it was purified and then dissolved in water. *L. dextranicum* NRRL-B-18132 was grown for 48 hours at 24° C. in 1 liter sucrose-salts medium. Two volumes of isopropanol were added to the culture and the solution and resulting precipitate were filtered through a Buchner funnel. The precipitate was then dried under vacuum and crushed into an off-white colored powder. The yield was approximately 45 g. This powder was rehydrated at 5% and 10% in distilled water. At 10% concentration, there was a great degree of viscosity evident by visual examination. At 5% concentration, there was still significant viscosity although less than at the 10% concentration.

EXAMPLE 3

Effects of initial sucrose concentration. The effects of varying the initial sucrose concentrations from 0–10% by weight in NFDM-sucrose growth medium were examined. The results are summarized in Table 1.

TABLE 1

| | Effects of Initial Sucrose Concentration on Final Acidities and Viscosities in NFDM-sucrose | | | |
|---|---|---|---|---|
| Bottle | % sucrose | Final pH[a] | Titrable acidity[b] | Viscosity/Time[c] |
| A | 0(no bacteria) | 6.45 | .26 | 11 sec. |
| B | 0 | 6.25 | .32 | 9 sec. |

TABLE 1-continued

Effects of Initial Sucrose Concentration on Final Acidities and Viscosities in NFDM-sucrose

| Bottle | % sucrose | Final pH[a] | Titrable acidity[b] | Viscosity/Time[c] |
|---|---|---|---|---|
| C | 2 | 5.17 | .68 | 21 sec. |
| D | 3 | 5.15 | .65 | 51 sec. |
| E | 4 | 5.12 | .63 | >2 min. |
| F | 5 | 5.16 | .58 | >2½ min. |
| G | 6 | 5.20 | .49 | >2½ min. |
| H | 7 | 5.20 | .51 | >2½ min. |
| I | 8 | 5.20 | .50 | >3 min. |
| J | 9 | 5.21 | .48 | >3 min. |
| K | 10 | 5.21 | .53 | >3 min. |

[a] After growth at 32° C. for 18 hrs. with an initial inoculum of $10^8$ cfu/ml

[b] $\% \text{ TA} = \frac{\text{ml of 0.1N NaOH} \times \text{meq lactic acid}}{\text{wt. sample}} \times 100$

[c] Time required for 10 ml solution to flow through a glass 10 ml pipet.

By a crude method of measuring viscosity by flow through a glass 10 ml pipet, it appeared that viscosity increased sharply in the range of 4-5% initial sucrose concentration. Also, the highest acidities occurred in the range of 2-5% initial sucrose concentration which suggested that higher amounts of sucrose slightly inhibited the growth of L. dextranicum in this medium.

EXAMPLE 4

Effects of time of growth on polysaccharide production. L. dextranicum NRRL-B-18132 was grown in four separate flasks containing 100 ml sucrose-salts medium. Growth was terminated at 18 hrs, 24 hrs, 40 hrs, and 48 hrs by the addition of 200 ml isopropanol. The solutions and precipitates were filtered through a Buchner funnel, dried under vacuum, and the precipitates were weighed. The 18 hr precipitate was 2.3 g but was spongy and sticky in texture indicating residual sucrose and inefficient drying. The 24 hr precipitate wighed 2.1g and showed the same consistency. The 40 hr precipitate was 2.4 g and appeared to dry well as did the 2.5 g 48 hrs precipitate. These results indicated that growth should continue beyond 24 hrs to eliminate residual sucrose and improve yields.

EXAMPLE 5

Effects of initial amounts of milk solids on polysaccharide production. Fifteen percent (15%) by weight non-fat dry milk (NFDM) was diluted to 12.5, 10, 7.5 and 5.0% milk solids and sucrose was added to a 10% by weight final concentration for each. L. dextranicum NRRL-B-18132 cells were added at $4.6 \times 10^7$ starting cell count per ml. The results after 48 hours of incubation at 32° C. indicated that the initial percent milk solids could be dropped from 15% to 10% without any noticeable loss in viscosity.

EXAMPLE 6

Effects of various inoculation rates on viscosity. NFDM-sucrose (15%-10%) media were inoculated with the following cell counts of L. dextranicum per ml: $4.75 \times 10^7$, $9.5 \times 10^7$, $1.9 \times 10^8$, and $5.6 \times 10^8$. The cultures were then grown at 32° C. for 24 hours. The results are summarized in Table 2. Measurements indicated that inoculation rates above $10^8$/ml gave excellent viscosity after 24 hours incubation at 32° C.

TABLE 2

Effects of inocula upon final culture viscosities.

| Bottle | Initial Cell Count[b] | Final pH[a] | Final Cell Count[b] | Viscosity/Time[c] |
|---|---|---|---|---|
| A | $4.75 \times 10^7$ | 5.78 | $2 \times 10^8$ | 20 sec. |
| B | $9.5 \times 10^7$ | 5.40 | $5 \times 10^8$ | >1 min. |
| C | $1.9 \times 10^8$ | 4.85 | $1.3 \times 10^9$ | Unmeasurable[d] |
| D | $5.6 \times 10^8$ | 4.56 | $1.4 \times 10^9$ | Unmeasurable[d] |

[a] After growth at 32° C. for 24 hours
[b] CFU/ml
[c] Time required to flow through a Zahn viscometer #4
[d] Would not flow through a Zahn #4 cup

SUMMARY

Various aspects of polysaccharide synthesis by L. dextranicum NRRL-B-18132 have been described. Three media were used successfully at 25° and 32° C. Scale ups to one liter and ten liters were accomplished. The best polysaccharide yields were obtained after growth at 32° C. for 48 hrs. A procedure for purification of the polysaccharides from the sucrose-salts medium was worked out and these dextrans were used in viscosity tests. The hydration capacity of the material dried with milk solids appeared to be very good.

The pH of the dried product and the growth medium was about pH 5.3 where there was no neutralization during growth of the Leuconostoc dextranicum. Preferably the pH was between about 5.2 and 5.4. These bacteria are relatively poor producers of acid. In any event, the growth medium can be neutralized during the fermentation.

Food applications

Several applications in dairy foods were investigated and are demonstrated in the following examples. The dextrans can be used in various other food products.

EXAMPLE 7

Use of Polysaccharide Powder as a Thickener in Milk Drinks.

Spray-dried powder (about 2 to 3 percent moisture) from a Leuconostoc dextranicum NRRL-B-18132 culture grown in non-fat dry milk-sucrose medium (10% sucrose and 15% NFDM, where the NFDM and sucrose was steamed at 95° C for 30 minutes) was reconstituted to 26% w/v in distilled water. The 26% solids level was determined from the fermented growth medium just prior to spray-drying using a hand held refractometer. The powder (130g) was rehydrated in 500 ml of distilled water and percent solids were reconfirmed using the refractometer. A control consisting of 26% by weight milk solids was also prepared.

The ingredients were mixed using a Waring blender at low speed. Frozen orange juice concentrate (180g) was added and again blended at low speed until completely dispersed. The mixtures were then chilled in an ice bath and held until tasting.

The spray dried polysaccharide mixture did not appear very viscous immediately after mixing. After about one hour, the viscosity increased markedly. The 26% w/v milk control was not viscous at all. Taste testing of the orange milk drink gave favorable results as most individuals liked both the flavor and texture of the milk drink. The pH of the aqueous polysaccharide mixture before addition of the orange juice concentrate was 6.2 and after addition was 4.8. Two other flavors, strawberry and chocolate (addition of frozen, unsweetened strawberries or chocolate syrup), also gave favorable results. The viscosity of the drinks was not only maintained after a week of refrigeration at 4° C., but actually increased. It was concluded that the reconstituted milk and polysaccharide powder mixture was useful in flavored milk drinks as a thickener conferring body.

EXAMPLE 8

Use of Polysaccharide Powder as a Major Ingredient in Salad Dressing.

Spray dried powder (about 2 to 3 percent moisture) from *Leuconostoc dextranicum* NRRL-B-18132 culture grown in nonfat dry milk-sucrose medium as in Example 6 (10% sucrose and 15% NFDM by weight) was reconstituted to 23% by weight solids in distilled water to a final volume of 500ml. The 23% by weight solids concentration was determined using a hand held refractometer. Twenty percent (20%) (vol/vol) reconstituted lemon juice and 4% (vol/vol) olive oil were added along with the following seasonings: 2mg/ml oregano (about 1.0 g) 4 mg/ml garlic powder (about 2.0 g), and 4 mg/ml seasoning salt (about 2.0 g). The ingredients were mixed in a blender at low speed for 2 minutes.

The salad dressing made from the powder exhibited good viscosity and coating capacity. Viscosity increased upon storage at 4° C. The spices remained well suspended after storage and the flavor was good. The final pH was 4.01 which is desirable. It was concluded that the spray dried powder containing the polysaccharides was useful as a thickening agent for salad dressings.

EXAMPLE 9

Use of Polysaccharide Powder as a Major Ingredient in ice milk.

Spray dried powder (about 2 to 3 percent moisture) from *Leuconostoc dextranicum* NRRL-B-18132 culture grown in nonfat dry milk-sucrose medium (10% sucrose and 15% NFDM by weight) as in Example 6 was reconstituted to 16% by weight solids in distilled water as determined using a hand held refractometer. Two cups of this reconstituted powder were added to one cup sucrose and mixed with light heating until dissolved. Another two cups of reconstituted powder were added to two cups of whipping cream and two tablespoons of vanilla. All ingredients were then mixed together and processed in an ice cream freezer.

The ice milk product displayed a light, fluffy texture and creamy mouth feel with no formation of ice crystals. The final pH was 5.8 with a titratable acidity of 0.38% expressed as lactic acid.

The spray dried polysaccharide powder is useful as a texture improver for frozen milk products. The recipe of this Example eliminates half the whipping cream and all of the milk from the conventional ice cream recipe resulting in less calories and fat in the final product with a good creamy mouth feel.

The polysaccharide powder is also useful in the frozen yogurt industry since yogurt can be produced with reconstituted powder added along with the culture to produce the yogurt or can be added as a thickener or stabilizer to the finished yogurt.

Various diacetyl producing bacteria can be incorporated in the growth medium with the *Leuconostoc dextranicum*. This produces a buttery flavor in the dried composition which is desirable in some foods (e.g. whipped butter or margarine). *Streptococcus lactis* subspecies *diacetylactis* and *Leuconostoc citrovorum* can be used with good result. Citrate is usually added along with the milk solids which is metabolized to produce the diacetyl.

It is intended that the foregoing description be only illustrative of the present invention and that the present invention be limited only by the hereinafter appended claims.

We claim:

1. A food product which comprises in admixture:
   (a) a food which is a mixture of ingredients and
   (b) a quality improving amount of a dried composition which comprises in admixture a drying aid and polysaccharides derived by fermenting an aqueous growth medium comprising sucrose with a Leuconostoc dextranicum which produces the polysaccharides which are substantially rehydratable from the sucrose until the sucrose is substantially depleted and then drying the aqueous mixture to a powder with the drying aid, wherein the quality improvement is in thickness, stability or texture of the food product.

2. The food product of claim 1 wherein in addition a diacetyl producing bacterium is fermented in the growth medium to produce a diacetyl flavor in the composition and food.

3. The food product of claim 1 wheein the drying aid is milk solids.

4. The food product of claim 1 wherein the drying aid is selected from the group consisting of non-fat dry milk solids, skim milk and condensed milk.

5. The food product of claim 1 wherein the dried composition has been spray dried.

6. The food product of claim 3 wherein the dried composition contains between about 1 and 5 peroent by weight moisture before being admixed with the food.

7. The food product of claim 1 wherein the *Leuconostoc dextranicum* is NRRL-B-18132.

* * * * *

UNITED STATES PATENT AND TRADEMARK OFFICE
CERTIFICATE OF CORRECTION

PATENT NO. : 4,877,634
DATED : October 31, 1989
INVENTOR(S) : Michael J. Pucci and Blair S. Kunka It is certified that error appears in the above—identified patent and that said Letters Patent is hereby corrected as shown below:

Column 1, line 60 "is an energy" should read --as an energy--.

Column 1, line 62 after "sucrase", insert a period --.--.

Column 1, line 65 "recoer" should be --recover--.

Column 3, line 11 after "polysaccharides" insert a period --.--.

Column 3, line 15 after "moisture" insert a period --.--.

Column 4, line 36 "spray-died" should be --spray-dried--.

Column 8, line 41 "wheein" should be --wherein--.

Column 8, line 49 "peroent" should be --percent--.

Signed and Sealed this

Fifteenth Day of January, 1991

*Attest:*

HARRY F. MANBECK, JR.

*Attesting Officer*     *Commissioner of Patents and Trademarks*